(12) United States Patent
Hanchar et al.

(10) Patent No.: US 8,829,237 B2
(45) Date of Patent: Sep. 9, 2014

(54) PRODUCTION OF CARBOXYLIC ACID AND SALT CO-PRODUCTS

(75) Inventors: Robert J. Hanchar, Charlotte, MI (US); Susanne Kleff, Okemos, MI (US); Michael V. Guettler, Holt, MI (US)

(73) Assignee: The Michigan Biotechnology Institute, Lansing, MI (US)

( * ) Notice: Subject to any disclaimer, the term of this patent is extended or adjusted under 35 U.S.C. 154(b) by 449 days.

(21) Appl. No.: 13/039,913

(22) Filed: Mar. 3, 2011

(65) Prior Publication Data

US 2012/0225095 A1 Sep. 6, 2012

(51) Int. Cl.
| | |
|---|---|
| *C07C 51/02* | (2006.01) |
| *C07C 51/42* | (2006.01) |
| *C07C 55/02* | (2006.01) |
| *C07C 55/06* | (2006.01) |
| *C07C 55/10* | (2006.01) |
| *C07C 55/22* | (2006.01) |
| *C12P 7/46* | (2006.01) |
| *C12P 7/48* | (2006.01) |
| *C01F 5/14* | (2006.01) |
| *C01C 1/24* | (2006.01) |
| *C01D 1/04* | (2006.01) |
| *C01F 11/02* | (2006.01) |

(52) U.S. Cl.
CPC . *C01C 1/24* (2013.01); *C07C 51/02* (2013.01); *C01F 5/14* (2013.01); *C12P 7/46* (2013.01); *C01D 1/04* (2013.01); *C12P 7/48* (2013.01); *C01F 11/02* (2013.01)
USPC .......................................................... 562/593

(58) Field of Classification Search
CPC ........ C07C 51/02; C07C 51/42; C07C 55/02; C07C 55/06; C07C 55/10; C12P 7/46; C12P 7/48
USPC .......................................................... 562/593
See application file for complete search history.

(56) References Cited

U.S. PATENT DOCUMENTS

| | | | |
|---|---|---|---|
| 2,258,310 | A | 10/1941 | Abbott |
| 5,723,322 | A | 3/1998 | Guettler et al. |
| 5,958,744 | A | 9/1999 | Berglund et al. |
| 6,265,190 | B1 | 7/2001 | Yedur et al. |
| 2007/0015264 | A1 | 1/2007 | Isotani et al. |
| 2010/0297715 | A1 | 11/2010 | Dehay et al. |

FOREIGN PATENT DOCUMENTS

FR    WO 2009/081012    *    7/2009 ................ C12P 7/46

OTHER PUBLICATIONS

PCT/US2012/027450, PCT International Search Report, Form PCT/ISA/210, dated Aug. 9, 2012, 4 pgs.
PCT/US2012/027450, PCT Written Opinion, Form PCT/ISA/237, dated Aug. 9, 2012, 5 pgs.

* cited by examiner

*Primary Examiner* — Yevegeny Valenrod
(74) *Attorney, Agent, or Firm* — Marshall, Gerstein & Borun LLP

(57) ABSTRACT

This invention provide processes for producing carboxylic acid product, along with useful salts. The carboxylic acid product that is produced according to this invention is preferably a $C_2$-$C_{12}$ carboxylic acid. Among the salts produced in the process of the invention are ammonium salts.

19 Claims, 2 Drawing Sheets

PRODUCTION OF CARBOXYLIC ACID AND SALT CO-PRODUCTS

STATEMENT REGARDING FEDERALLY SPONSORED RESEARCH OR DEVELOPMENT

This invention was made with Government support under Grant No. DE-FG36-07GO87005, awarded by U.S. Department of Energy. The Government has certain rights in the invention.

FIELD OF THE INVENTION

This application relates to the production of carboxylic acid and salt co-product. In particular, the invention relates the production of carboxylic acid and ammonium salt.

BACKGROUND

Fermentation processes generally produce end products that need to be separated and/or recovered for further use. In many fermentation processes in which organic acids are produced, for example, a base is added to maintain the desired pH as the organic acids are produced. The addition of the base converts the acid to its salt form. Stronger acids such as mineral acids are added to convert the salt form of the organic acid back to its acid form and to facilitate the separation and recovery of the organic acid product. This series of treatments can produce a variety of salt by-products, at least some of which may have to be discarded as undesirable waste.

U.S. Patent Publication 2007/0015264 discloses the production of ammonium salts of organic acids. The ammonium salt composition is produced by fermenting a carbohydrate in the presence of a magnesium compound to produce a magnesium salt of an organic acid. The magnesium salt composition that is produced is treated with an ammonium base to produce the ammonium salt of the organic acid and a magnesium base, which can be used in subsequent fermentations, but leaves the organic acid in the ammonium salt form.

U.S. Pat. No. 5,598,744 discloses a process for producing succinic acid from a succinate salt. The method involves the formation of diammonium succinate, either by using an ammonium ion based material to maintain neutral pH in the fermentor or by substituting the ammonium cation for the cation of the succinate salt created in the fermentor. The diammonium succinate is reacted with a sulfate ion, such as by combining the diammonium succinate with ammonium bisulfate and/or sulfuric acid at sufficiently low pH to yield succinic acid and ammonium sulfate. The ammonium sulfate is advantageously cracked thermally into ammonia and ammonium bisulfate. The succinic acid can be purified with a methanol dissolution step. Various filtration, reflux and reutilization steps can also be employed.

It would be desirable to find alternative or additional processes of producing organic acids such that co-production of salt compounds are reduced or that co-produced salt compounds are in a form that reduces undesirable waste. It would be further desirable to produce organic acids using a process in which the organic acid is relatively easy to separate and recover. It would also be desirable to enhance the quantity of acid produced relative to any salt co-product that may also be produced.

SUMMARY OF THE INVENTION

This invention provides a process for producing carboxylic acid and a salt co-product in a form which can be used in a variety of purposes, including but not limited to fertilizer, thereby reducing waste from the overall process. The process further enables the acid to be produced in a relatively high quantity. The acids that are produced can also be relatively easily separated and recovered.

According to one aspect of the invention, there is provided a process for producing carboxylic acid and ammonium salt. The process can include a step of providing an aqueous solution containing at least one alkali metal or alkaline earth metal salt of a carboxylic acid. Alternatively, the process can include a step of fermenting a carbohydrate in the presence of at least one alkali metal or alkaline earth metal salt to produce at least one alkali metal or alkaline earth metal salt of a carboxylic acid.

The least one alkali metal or alkaline earth metal salt of a carboxylic acid can be treated with an inorganic acid to convert at least a portion of the least one alkali metal or alkaline earth metal salt of a carboxylic acid to its carboxylic acid form and produce a water soluble alkali metal or alkaline earth metal salt.

The carboxylic acid is separated from the water soluble alkali metal or alkaline earth metal salt, and the water soluble alkali metal or alkaline earth metal salt is treated with ammonia, ammonium hydroxide, ammonium carbonate or ammonium bicarbonate to produce an ammonium salt and an alkali metal or alkaline earth metal precipitate.

The alkali metal can be represented by at least one metal selected from the group consisting of lithium, sodium, potassium, rubidium, cesium, and francium.

The alkaline earth metal can be represented by at least one metal selected from the group consisting of beryllium, magnesium, calcium, strontium, barium, and radium.

In one embodiment, the provided aqueous solution contains a magnesium salt of a carboxylic acid.

The carboxylic acid can be a dicarboxylic acid or a tricarboxylic acid.

In one embodiment, the inorganic acid is comprised of a sulfur-containing anion or nitrogen containing anion. A particular inorganic acid can be sulfuric acid.

In one embodiment, the ammonium salt is ammonium sulfate.

The process can further include a step of separating the ammonium salt from the alkali metal or alkaline earth metal precipitate. At least a portion of the alkali metal or alkaline earth metal precipitate can be added to a fermentation medium to form the at least one alkali metal or alkaline earth metal salt of a carboxylic acid.

In one embodiment of the invention, the alkali metal or alkaline earth metal precipitate is magnesium hydroxide.

In another embodiment, the fermentation medium comprises at least one carboxylic acid producing organism and carbohydrate.

BRIEF DESCRIPTION OF THE DRAWINGS

Examples of various preferred embodiments of this invention are shown in the attached Figures, wherein.

DETAILED DESCRIPTION OF THE INVENTION

Figure 1:
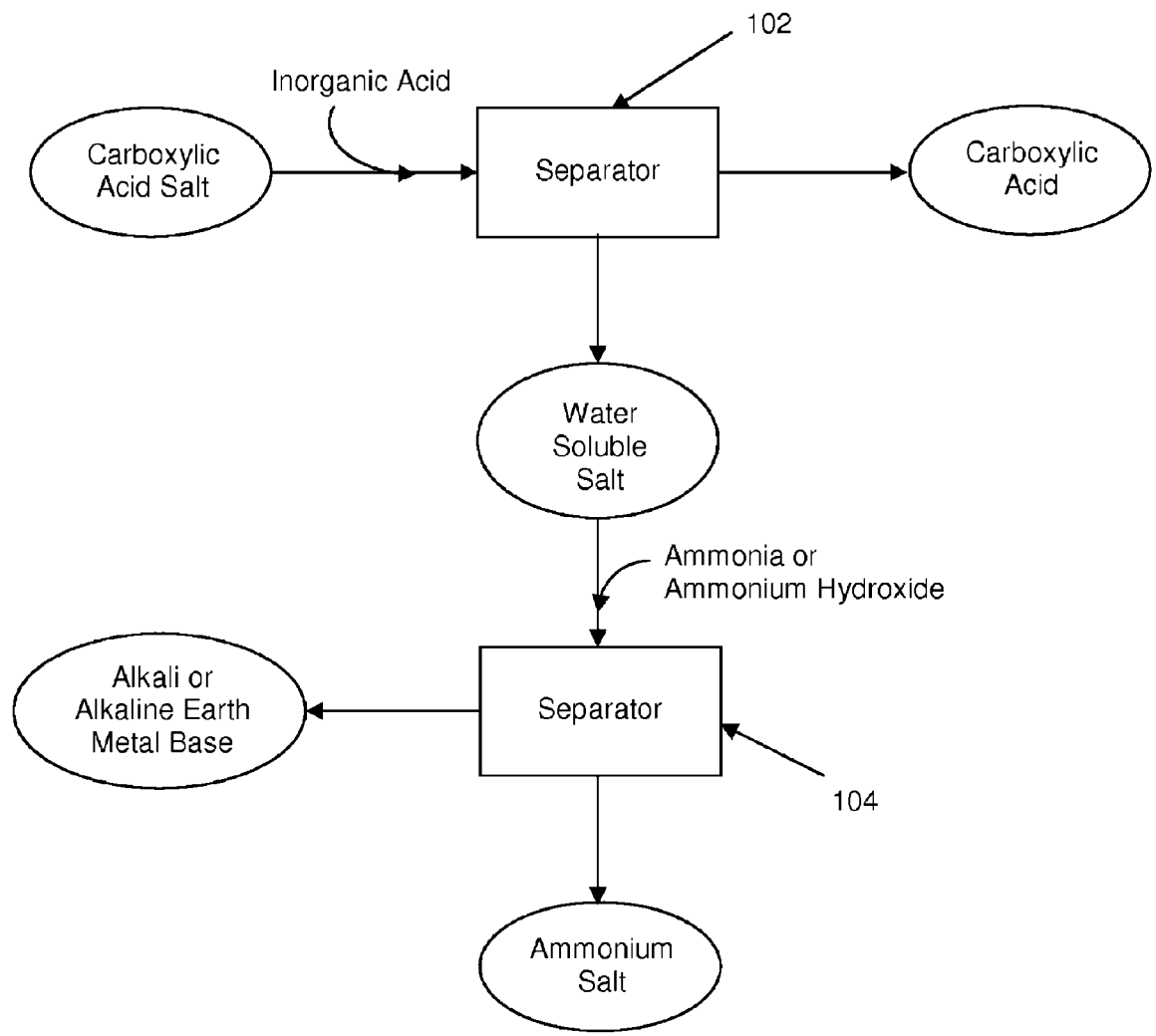
FIG. 1 is a process flow diagram showing a process of treating an aqueous solution of a carboxylic acid salt to produce carboxylic acid and ammonium salt co-product.

I. Production of Carboxylic Acid and Ammonium Salt

This invention provides a process for producing carboxylic acid product, along with useful salts. The acid product can be produced at a relatively high concentration, and the salts that are co-produced in the process have a wide variety of uses.

The carboxylic acid product that is produced according to this invention is a $C_2$-$C_{12}$ carboxylic acid. In one embodiment, the carboxylic acid is a dicarboxylic acid or a tricarboxylic acid, preferably a dicarboxylic acid, more preferably a $C_4$ dicarboxylic acid. The carboxylic acid can be saturated or unsaturated, branched or linear, substituted (e.g., hydroxyl substituted or amino substituted) or unsubstituted.

Examples of dicarboxylic acids include, but are not limited to, oxalic acid, malonic acid, succinic acid, fumaric acid, maleic acid, malic acid, tartaric acid, aspartic acid, glutaric acid, glutamic acid, glutaconic acid, adipic acid, muconic acid, suberic acid, itaconic acid, and terephthalic acid. Examples of tricarboxylic acids include, but are not limited to, citric acid, isocitric acid, aconitic acid, propane-1,2,3-tricarboxylic acid, and trimesic acid.

Among the salts produced in the process of the invention are ammonium salts. Examples of ammonium salts that are produced include, but are not limited to ammonium sulfate, ammonium nitrate, mono-ammonium phosphate, di-ammonium phosphate, ammonium chloride, tri-ammoniumphosphate, ammonium sulfate and mixtures thereof.

The ammonium salts that are produced in the process of the invention are beneficial in that they have a variety of uses. Examples of uses of the ammonium salts include, but are not limited to, a fertilizer or fertilizer component; an adjuvant for insecticides, herbicides and fungicides; an additive in vaccines; as a nutrient source in other fermentations; a food additive; and a flame retardant.

II. Carbon Source for Producing Carboxylic Acid

The carboxylic acids that can be produced according to this invention are ultimately derived from alkali metal or alkaline earth metal salts of carboxylic acids. Examples of the alkali metal portion of the alkali metal carboxylic acids that can be used as a part of the process of this invention include at least one metal selected from the group consisting of lithium, sodium, potassium, rubidium, cesium, and francium. Examples of the alkaline earth metal portion of the alkaline earth metal carboxylic acids that can be used as a part of the process of this invention include at least one metal selected from the group consisting of beryllium, magnesium, calcium, strontium, barium and radium.

In practice, the carboxylic acid products produced according to the invention are derived from a carbon source in which the carbon source is fermented in an appropriate fermentation medium. Although the fermentation will produce a carboxylic acid in its acid form, the fermentation is preferably carried out in the presence of, or with the addition of, one or more bases containing the alkali metal or alkaline earth metal to control pH within a range that enhances carboxylic acid production. As a result of carrying out the fermentation in the presence of at least one of an alkali metal or alkaline earth metal bases, an alkali metal or alkaline earth metal salt of the carboxylic acid forms in the fermentation medium. It is this carboxylic acid salt that is treated to ultimately produce the desired carboxylic acid in its acid form, as well as producing a salt containing the alkali or alkaline earth metal. Subsequently, this alkali or alkaline earth metal salt is then treated to form an alkali or alkaline earth metal base, and salt co-products that have a variety of end uses.

The fermentable carbon source used in the practice of this invention can be any carbohydrate that is fermented by a microorganism that is used to form the desired acid product of this invention. The term ferment, fermenting or fermentable is considered to generally refer to an enzymatically controlled transformation of an organic compound, e.g. fermentable carbon source. Such a fermentable carbon source or carbohydrate source includes any one or more of glucose, sucrose, fructose, lactose, soluble starches, pentoses, glycerol, polyols, crude biomass hydrolysates, corn syrups, and cane and beet molasses.

The concentration of carbohydrate in the fermentation medium should be sufficiently high to form sufficient quantity of the desired acid product, but not so high as to impede the fermentation process itself. In one embodiment, the concentration of fermentable carbon source in the fermentation medium is from about 20 g/l to about 250 g/l, preferably from about 100 g/l to about 160 g/l.

III. Fermenting Step

The fermenting step that can be included as a part of this invention incorporates the use of a microorganism that produces the desired carboxylic acid product. In one embodiment, the fermentation process incorporates the use of a microorganism that actively expresses at least one enzyme selected from the group consisting of aconitase, isocitrate dehydrogenase, α-ketoglutarate dehydrogenase, succinate dehydrogenase, fumarase, malate dehydrogenase, citrate synthase, lactate dehydrogenase, pyruvate carboxylase, phosphoenolpyruvate carboxykinase, phosphoenolpyruvate carboxylase, fumarate reductase and malic enzyme. One or more of these enzymes can be used to convert the fermentable carbon source directly or indirectly to the desired carboxylic acid product.

Any organism that naturally expresses one or more of the enzymes used in converting feed into one or more of the acid compositions produced according to the process of this invention can be used. Such organisms include, but are not limited to bacteria such as *Escherichia coli, Bacillus subtilis*, lactobacilli, bacilli, cocci, and coccobacilli including *Actinobacillus succinogenes* and related acid producing species in the Pasteurellaceae family; also including yeasts, other fungi, filamentous fungi, including acid producing species of *Rhizopus* and *Aspergillus*.

The fermenting step is carried out in a fermentation medium, preferably an aqueous medium. In a preferred embodiment, fermenting is carried out in the presence of an alkali metal or alkaline earth metal base, preferably a magnesium compound that contains at least one oxygen atom. More preferably, the fermenting is carried out in the presence of an alkaline earth metal base, most preferably a magnesium compound selected from the group consisting of magnesium oxide, magnesium hydroxide, magnesium bicarbonate and magnesium carbonate.

Examples of additional alkali or alkaline earth metal bases that can also be used include lithium hydroxide, lithium carbonate, lithium bicarbonate, sodium hydroxide, sodium carbonate, sodium bicarbonate, potassium hydroxide, potassium carbonate, potassium bicarbonate, calcium hydroxide, calcium carbonate, calcium bicarbonate, barium hydroxide, barium carbonate, barium bicarbonate and mixtures thereof.

In one embodiment, the fermenting step is carried out so that the fermentation medium is maintained at a pH of at least 4, more preferably at least 5, and most preferably at least 6. In another embodiment, fermenting is carried out at a pH of not greater than 8.5, preferably not greater than 7.5, more preferably not greater than 7.2. In yet another embodiment, fermenting is carried out at a pH of from 5 to 8, more preferably from 6 to 7.

In another embodiment, the alkali metal or alkaline earth metal salt is added to the fermentation medium at a rate sufficient to maintain the fermentation medium at the desired pH. In a particularly preferred embodiment, magnesium carbonate or magnesium hydroxide, most preferably magnesium hydroxide, is added to the fermentation medium at a rate sufficient to maintain the fermentation medium at the desired pH.

In yet another embodiment of the invention, the fermenting step is carried out with oxygen (including in the form of air), carbon dioxide or both being added to the fermentation medium. Carbon dioxide can be supplied to the fermentation medium in various ways. For example, carbon dioxide can be added to the medium as part of the alkali or alkaline earth metal base as a mineral carbonate or bicarbonate form, in air, in $CO_2$ enriched air, or directly as pure or substantially pure $CO_2$. In one embodiment a fluid, preferably a gas, containing $CO_2$ is added to the fermentation medium. Preferably, the fluid contains at least 0.05% $CO_2$, more preferably from 0.1% to 60% $CO_2$, based on total volume of the fluid added to the medium. More preferably, the fluid contains from 0.2% to 30% $CO_2$, and most preferably from 0.4% to 15% $CO_2$, based on total volume of the fluid or gas added to the medium. In another embodiment, gas, i.e., a total gas addition that includes $CO_2$, is supplied or added to the medium at a total gas volume rate per volume of fermentation medium of from 0.3 l/l-min to 1.3 l/l-min, preferably from 0.5 l/l-min to 1.0 l/l-min. The gas can be added to the medium from one or more sources. During addition of the $CO_2$, the medium is preferably maintained at a predetermined or preferred pH. In particular, pH can be controlled at the predetermined level by the addition of the alkali or alkaline earth metal base, and more preferably by addition of a magnesium compound that contains oxygen.

In one embodiment, the fermenting step is carried out in a pressurized reactor that contains carbon dioxide at superatmospheric pressure. The carbon dioxide can be mixed with other gases as long as the gases employed do not interfere with the growth and metabolism of the organism employed. Carbon dioxide can also be supplied to the fermentation medium by the addition of carbonates or bicarbonates which may generate this gas under the conditions of the fermentation. The fermentation medium preferably contains dissolved $CO_2$ in equilibrium with a minimum of about 0.1 atmosphere partial pressure of carbon dioxide. In a particular embodiment, the fermentation medium is saturated with carbon dioxide and the atmosphere contains at least about 0.3 atmosphere partial pressure of carbon dioxide.

IV. Separation of Acid Salt from Fermentation Liquor

The carboxylic acid salt composition that is formed in the fermenting step is preferably separated from at least a portion of the fermentation liquor. As used herein, the term fermentation liquor refers to the entire fermented composition. This would include liquid as well as solid components in the fermentation vessel. In an embodiment, a liquid portion is separated from the liquor in which the separated liquid portion contains at least a majority of the carboxylic acid salt originally included in the fermentation liquor.

The carboxylic acid salt can be separated from the liquor using any suitable means. For example, separation can be accomplished using such means as a clarifier, filter, or centrifuge. Any suitable alternative means can be used.

V. Treating Carboxylic Acid Salt with Inorganic Acid

This invention includes a treatment step in which at least one alkali metal or alkaline earth metal salt of a carboxylic acid is treated with an inorganic acid to convert at least a portion of the least one alkali metal or alkaline earth metal salt of a carboxylic acid to its carboxylic acid form and produce a water soluble alkali metal or alkaline earth metal salt. According to this invention, a water soluble alkali metal or alkaline earth metal salt is defined as a salt that will remain in solution when at least a portion of the organic acid product precipitates or separates from the acidified liquid portion at any temperature and concentration level. Preferably the inorganic salt will remain in solution at a temperature and concentration level where a majority of the desired organic acid separates or precipitates.

In one embodiment of the invention, a carboxylic acid is produced in which the carboxylic acid has more than one pKa. Preferably, the salt form of the carboxylic acid is converted to its acid form by treating with an inorganic acid to reduce pH of the liquid portion to below at least a first pKa of the acid form of the organic acid product to convert at least a portion of the least one alkali metal or alkaline earth metal salt of the carboxylic acid to its carboxylic acid form and produce a water soluble alkali metal or alkaline earth metal salt.

Examples of inorganic acids that can be used in this treatment step include, but are not limited to, hydrochloric acid, phosphoric acid, nitric acid and sulfuric acid. Preferably, sulfuric acid or nitric acid is used as the inorganic acid.

An amount of the inorganic acid is added that is sufficient to convert at least a portion of the carboxylic acid salt to the free acid. Preferably enough inorganic acid is added to convert a majority (i.e., at least 50%) of the carboxylic acid salt to its free acid form. Typically between 0.1 and 10 molar equivalents of inorganic acid are added compared to the amount of carboxylate salt. More preferably 0.5 to 5 molar equivalents are added, and most preferably between 1 and 2 molar equivalents compared to the amount of carboxylate salt are added.

The particular water soluble alkali metal or alkaline earth metal salt that is formed during this treatment step will depend on the type of alkali metal or alkaline earth metal cation that is associated with the carboxylic acid that is being treated and the type of anion that is associated with the inorganic acid used. For example, in an embodiment in which a magnesium carboxylic acid salt is treated with inorganic acids selected from the group consisting of sulfuric acid, nitric acid or hydrochloric acid, the magnesium carboxylic acid salt will be converted to its carboxylic acid form, and water soluble magnesium sulfate, nitrate or chloride salt will be produced.

In another embodiment, lithium carboxylic acid salt is treated with inorganic acids selected from the group consisting of sulfuric acid, nitric acid or hydrochloric acid, the lithium carboxylic acid salt will be converted to its carboxylic acid form, and water soluble lithium sulfate, nitrate or chloride salt will be produced.

In another embodiment, sodium carboxylic acid salt is treated with inorganic acids selected from the group consisting of sulfuric acid, nitric acid or hydrochloric acid, the sodium carboxylic acid salt will be converted to its carboxylic acid form, and water soluble sodium sulfate, nitrate or chloride salt will be produced.

In another embodiment, potassium carboxylic acid salt is treated with inorganic acids selected from the group consisting of sulfuric acid, nitric acid or hydrochloric acid, the potassium carboxylic acid salt will be converted to its carboxylic acid form, and water soluble potassium sulfate, nitrate or chloride salt will be produced.

In another embodiment, calcium carboxylic acid salt is treated with inorganic acids selected from the group consisting of, nitric acid or hydrochloric acid, the calcium carboxylic acid salt will be converted to its carboxylic acid form, and water soluble calcium, nitrate or chloride salt will be produced.

In another embodiment, barium carboxylic acid salt is treated with inorganic acids selected from the group consisting of, nitric acid or hydrochloric acid, the barium carboxylic acid salt will be converted to its carboxylic acid form, and water soluble barium, nitrate or chloride salt will be produced.

VI. Separating Carboxylic Acid from Water Soluble Salt

Following treating the alkali metal or alkaline earth metal salt of the carboxylic acid with the inorganic acid to convert carboxylic acid salt to its carboxylic acid form and produce the water soluble alkali metal or alkaline earth metal salt, the carboxylic acid and water soluble salt are separated. Any suitable means can be used to separate the compounds. Examples of such means include, but are not limited to filtration, centrifugation, phase separation and sedimentation.

Typically, during acid treatment or lowering of the pH of the liquid portion to form the acid from the organic salt, the liquid portion increases in temperature. It is preferred to cool the treated liquid portion. In particular, it is preferred to reduce the temperature of the treated liquid portion to precipitate the desired acid product. In one embodiment, the treated liquid portion is reduced to a temperature of not greater than 40° C., preferably not greater than 30° C., more preferably not greater than 20° C., still more preferably not greater than 10° C., and most preferably not greater than 5° C.

VII. Treating Water Soluble Salt with Ammonia or Ammonium Ion Composition

The water soluble salt that is separated from the carboxylic acid is treated with an ammonium compound (i.e., an ammonium ion-containing base) to produce an ammonium salt and an alkali metal or alkaline earth metal precipitate. Examples of ammonium ion-containing bases or compounds that can be used are ammonia, ammonium hydroxide, ammonium carbonate and ammonium bicarbonate.

An amount of ammonium compound is added to convert at least a portion of the inorganic salt to its base and the corresponding ammonium salt. Preferably, enough ammonium compound is added to convert a majority (i.e., at least 50%) of the inorganic salt. For example, from 1 to 40 molar equivalents of ammonium compound is added relative to the inorganic acid salt. Preferably, from 5 to 20 are added or from 10 to 20 molar equivalents, relative to the inorganic acid salt.

The alkali metal or alkaline earth metal precipitate that is produced is sufficiently insoluble in water such that separation and recovery of the precipitate are more easily facilitated. Preferably, the alkali metal or alkaline earth metal precipitate has solubility in water of not greater than 25 g of precipitate per 100 g of water, more preferably not greater than 10 g, or greater than 0.1 g, of precipitate per 100 g of water.

In one embodiment of the invention, the alkali metal or alkaline earth metal precipitate incorporates magnesium as the metal component. Examples of the precipitated salt, therefore, include magnesium hydroxide, magnesium carbonate and magnesium bicarbonate.

In another embodiment of the invention, the alkali metal or alkaline earth metal precipitate incorporates lithium as the metal component. Examples of the precipitated salt, therefore, include lithium hydroxide, lithium carbonate and lithium bicarbonate.

In another embodiment of the invention, the alkali metal or alkaline earth metal precipitate incorporates sodium as the metal component. Examples of the precipitated salt, therefore, include, sodium carbonate and sodium bicarbonate.

In another embodiment of the invention, the alkali metal or alkaline earth metal precipitate incorporates potassium as the metal component. Examples of the precipitated salt, therefore, include potassium carbonate and potassium bicarbonate.

In another embodiment of the invention, the alkali metal or alkaline earth metal precipitate incorporates calcium as the metal component. Examples of the precipitated salt, therefore, include calcium hydroxide, calcium carbonate and calcium bicarbonate.

In another embodiment of the invention, the alkali metal or alkaline earth metal precipitate incorporates barium as the metal component. Examples of the precipitated salt, therefore, include barium hydroxide, barium carbonate and barium bicarbonate.

VIII. Recycle of Precipitate

In a preferred embodiment of the invention, the alkali metal or alkaline earth metal precipitate is used as the base or part of the base in the fermentation medium that is used to produce the desired carboxylic acid product. For example, at least a portion of the alkali metal or alkaline earth metal precipitate is applied in the fermenting step as the at least one alkali metal or alkaline earth metal base that is used to maintain or control pH.

IX. Examples

FIG. 1 shows an example of the process of this invention. According to FIG. 1, an aqueous solution containing at least one alkali metal or alkaline earth metal salt of a carboxylic acid is treated with an inorganic acid to convert at least a portion of the least one alkali metal or alkaline earth metal salt of a carboxylic acid to its carboxylic acid form and produce a water soluble alkali metal or alkaline earth metal salt. The carboxylic acid is separated from the water soluble salt in a separator 102. The separated water soluble alkali metal or alkaline earth metal salt is then treated with ammonia or ammonium hydroxide to produce an ammonium salt and an alkali metal or alkaline earth metal base precipitate. The ammonium salt is then separated from the alkali or alkaline earth metal base salt by way of separator 104.

Figure 2:
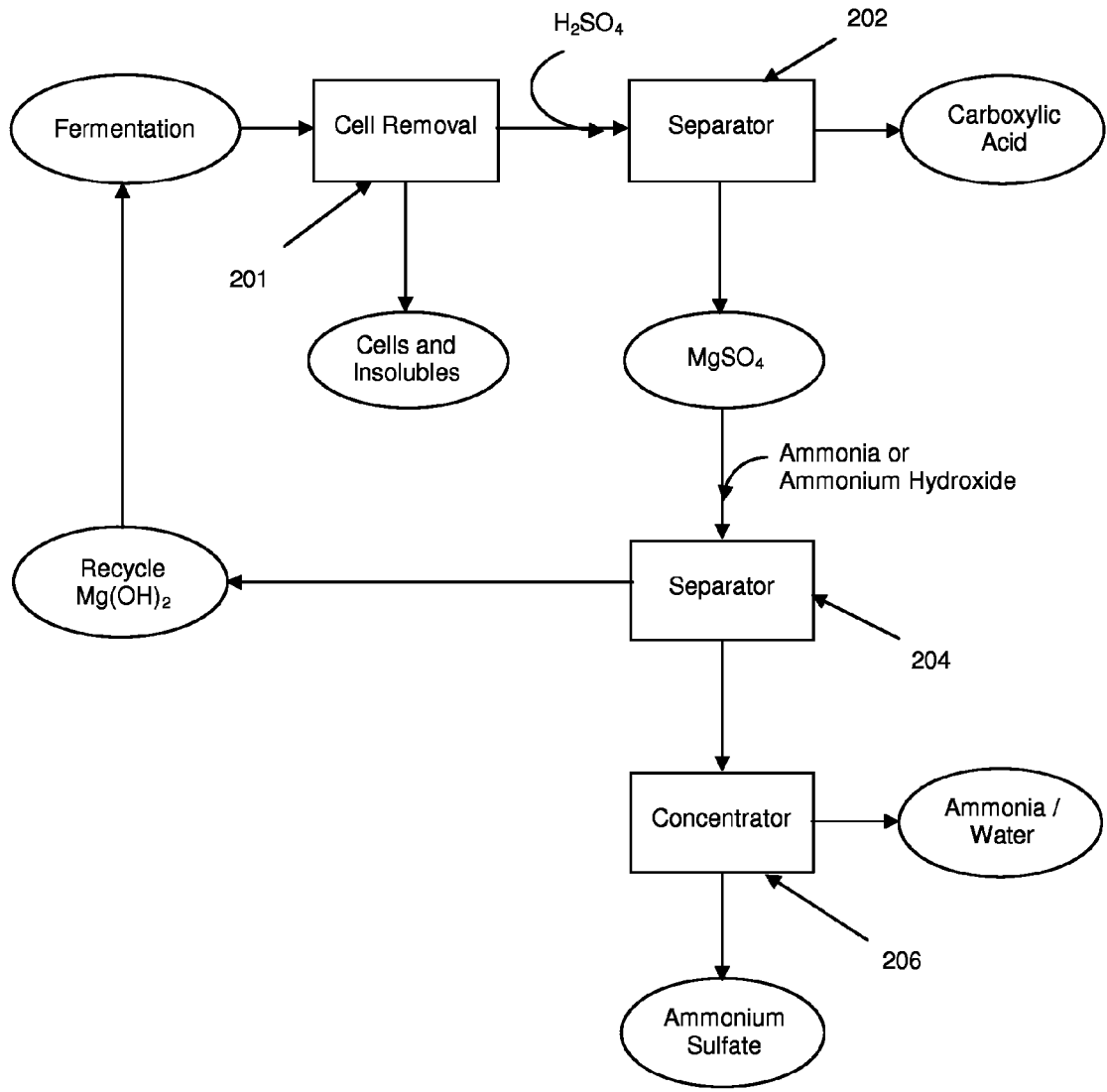
FIG. 2 is a process flow diagram showing a preferred process of producing an organic acid using a magnesium salt, recycling at least a portion of the magnesium salt, and separating ammonium sulfate that is also produced in the process.

FIG. 2 shows a preferred embodiment of the invention. According to FIG. 2, an organic acid such as succinic or fumaric acid is produced by fermenting a carbohydrate in the presence of at least one alkali metal or alkaline earth metal salt, preferably $Mg(OH)_2$ or $MgCO_3$, to produce at least one alkali metal or alkaline earth metal salt of the carboxylic acid. The carboxylic acid salt is then separated from cellular and other insoluble material in a separator 201, such as a centrifugal separator. The separated carboxylic acid salt is then treated with an inorganic acid, such as $H_2SO_4$, to convert at least a portion of the carboxylic acid salt to its carboxylic acid form and to produce a water soluble alkali metal or alkaline earth metal salt, such as $MgSO_4$.

The carboxylic acid is separated from the water soluble alkali metal or alkaline earth metal salt, e.g., $MgSO_4$, by way of separator 202, and the water soluble alkali metal or alkaline earth metal salt is treated with ammonia or ammonium hydroxide to produce an ammonium salt, e.g., $(NH_4)_2SO_4$, and an alkali metal or alkaline earth metal precipitate, e.g., $Mg(OH)_2$. The ammonium salt is separated from the precipitate by way of a separator 204. Preferably, the precipitate, e.g., $Mg(OH)_2$, is recycled to the fermentation step. The ammonium salt can be concentrated in a concentrator 206 to remove excess ammonia or ammonium hydroxide and water. Preferably, the ammonia and/or ammonium hydroxide is recycled to treat the water soluble alkali metal or alkaline earth metal salt, e.g., $MgSO_4$.

Example 1

Treatment of Water Soluble Salt with Ammonium Hydroxide

In a series of experiments, ammonium hydroxide was added to a water soluble alkali metal or alkaline earth metal salt, i.e., $MgSO_4$, to form ammonium sulfate and an alkali metal or alkaline earth metal precipitate, i.e., $Mg(OH)_2$. A matrix consisting of three starting concentrations of $MgSO_4$ and three levels of ammonium hydroxide were evaluated. The amount of Mg precipitated from the solution was determined by atomic absorption for Mg of the solution before addition of the ammonium hydroxide and after addition and filtering. The results from this matrix of experiments are shown in Table 1, showing that a surprisingly small percentage of the Mg ion was found in the solution, especially when excess ammonium hydroxide was used. Most of the Mg ion had precipitated.

TABLE 1

| Equivalents of $NH_4OH$ Used in Treatment | Wt % Mg in solution (i.e., metal sulfate salt) after treatment with $NH_4OH$ | | |
|---|---|---|---|
| | 5 wt % $MgSO_4$ solution | 10 wt % $MgSO_4$ solution | 20 wt % $MgSO_4$ solution |
| 5 | 28 | 21 | 20 |
| 10 | 12 | 11 | 15 |
| 20 | 11 | 8 | 11 |

As shown in the Table 2 below, alkali and earth alkaline metal cations have a higher pKa than ammonium ion, indicating that they form stronger bases, e.g., $Mg(OH)_2$ is a stronger base than $NH_4OH$, $Na_2CO_3$ is a stronger base than $(NH_4)_2CO_3$, etc.

TABLE 2 pKa values for ammonium and metal ions

| Ion | pKa value |
|---|---|
| $NH_4^+$ | 9.24 |
| $Na^+$ | 14.77 |
| $K^+$ | 16~16.5 |
| $Ca^{2+}$ | 12.8 |
| $Mg^{2+}$ | 11.41 |

Typically a weaker base will not react with a salt to form stronger base. Therefore the product composition for the reaction below would typically be expected to favor the components on the left side of the equation:

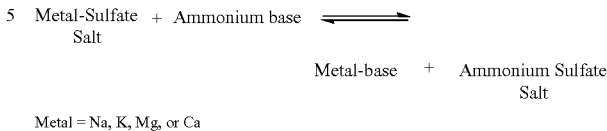

Metal-Sulfate + Ammonium base ⇌ Metal-base + Ammonium Sulfate Salt

Metal = Na, K, Mg, or Ca

The data in Table 1 shows that this does not hold true for the reaction of magnesium sulfate and ammonium hydroxide under all conditions. The majority of the magnesium sulfate reacts with the ammonium hydroxide to form ammonium sulfate and magnesium hydroxide, which precipitates from the solution, favoring the right side of the equation. The same or substantially the same results can also be expected from the group of alkali and alkaline earth metal and ammonium bases described previously, based on the data from Table 1.

Example 2

Recovery of $Mg(OH)_2$

To verify that the solid material collected from Example 1 was $Mg(OH)_2$, the base equivalents per gram of solid were determined by titration and compared to authentic $Mg(OH)_2$. The results are shown in Table 3, demonstrating the recoverable precipitate is a base, by exhibiting similar base equivalency as authentic $Mg(OH)_2$.

TABLE 3

| Solid ID | Equivalents $NH_4OH$ used in recovery | mEquiv. Base/g |
|---|---|---|
| $Mg(OH)_2$ | Not applicable | 35 |
| 50-AS | 20 | 35 |
| 50-BS | 10 | 33 |

The data in Table 3 demonstrates that the solid recovered is equivalent to magnesium hydroxide as a base. This further demonstrates that substantially all of the precipitate can be recycled in the overall fermentation process.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A process for producing carboxylic acid and ammonium salt, comprising:
   providing an aqueous solution containing at least one magnesium salt of a carboxylic acid;
   treating the at least one magnesium salt of a carboxylic acid with an inorganic acid to convert at least a portion of the at least one magnesium salt of a carboxylic acid to its carboxylic acid form and produce a water soluble magnesium salt;
   separating the carboxylic acid from the water soluble magnesium salt; and
   treating the water soluble magnesium salt with ammonia, ammonium hydroxide, ammonium carbonate, or ammonium bicarbonate to produce an ammonium salt and magnesium carbonate precipitate.

2. The process of claim 1, wherein the carboxylic acid is a dicarboxylic acid or a tricarboxylic acid.

3. The process of claim 1, wherein the inorganic acid is comprised of a sulfur-containing anion or nitrogen containing anion.

4. The process of claim 3, wherein the inorganic acid is sulfuric acid.

5. The process of claim 1, wherein the ammonium salt is ammonium sulfate.

6. The process of claim 1, further comprising separating the ammonium salt from the magnesium carbonate precipitate.

7. The process of claim 6, further comprising separating the magnesium carbonate from the ammonium salt and adding at least a portion of the separated magnesium carbonate precipitate to a fermentation medium to form the at least one alkali metal or alkaline earth metal salt of a carboxylic acid.

8. The process of claim 7, wherein the fermentation medium comprises at least one carboxylic acid producing organism and carbohydrate.

9. A process for producing carboxylic acid and ammonium salt, comprising:
fermenting a carbohydrate in the presence of at least magnesium carbonate to produce a magnesium salt of a carboxylic acid;
treating the magnesium salt of a carboxylic acid with an inorganic acid to convert at least a portion of the magnesium salt of a carboxylic acid to its carboxylic acid form and produce a water soluble magnesium salt;
separating the carboxylic acid from the water soluble magnesium salt; and
treating the water soluble magnesium salt with ammonia, ammonium hydroxide, ammonium carbonate, or ammonium bicarbonate to produce an ammonium salt and magnesium carbonate precipitate.

10. The process of claim 9, further comprising separating the ammonium salt from the magnesium carbonate precipitate and recycling the magnesium carbonate precipitate.

11. The process of claim 10, wherein recycling is carried out by adding at least a portion of the magnesium carbonate precipitate to the fermenting step.

12. The process of claim 9, wherein the carboxylic acid is a dicarboxylic acid or a tricarboxylic acid.

13. The process of claim 9, wherein the inorganic acid is comprised of a sulfur-containing anion or nitrogen containing anion.

14. The process of claim 13, wherein the inorganic acid is sulfuric acid.

15. The process of claim 1, wherein the water soluble magnesium salt is treated with 5 to 20 molar equivalents of ammonia, ammonium hydroxide, ammonium carbonate, or ammonium bicarbonate.

16. The process of claim 15, wherein the water soluble magnesium salt is treated with 10 to 20 molar equivalents of ammonia, ammonium hydroxide, ammonium carbonate, or ammonium bicarbonate.

17. The process of claim 9, wherein the water soluble magnesium salt is treated with 5 to 20 molar equivalents of ammonia, ammonium hydroxide, ammonium carbonate, or ammonium bicarbonate.

18. The process of claim 17, wherein the water soluble magnesium salt is treated with 10 to 20 molar equivalents of ammonia, ammonium hydroxide, ammonium carbonate, or ammonium bicarbonate.

19. The process of claim 9, further comprising recovering the magnesium carbonate precipitate and conducting a second step of fermenting a carbohydrate, wherein the second fermenting step is carried out in the presence of the recovered magnesium carbonate precipitate.

* * * * *